United States Patent [19]

Hubschwerlen et al.

[11] Patent Number: 4,699,986

[45] Date of Patent: Oct. 13, 1987

[54] IMINO COMPOUNDS USEFUL FOR MAKING β-LACTAMS

[75] Inventors: Christian N. Hubschwerlen, Durmenach, France; Gérard Schmid, Kienberg, Switzerland

[73] Assignee: Hofmann-La Roche Inc., Nutley, N.J.

[21] Appl. No.: 769,634

[22] Filed: Aug. 26, 1985

Related U.S. Application Data

[62] Division of Ser. No. 407,027, Aug. 11, 1982, Pat. No. 4,576,751.

[30] Foreign Application Priority Data

Aug. 27, 1981 [CH] Switzerland ............... 5524/81
Jun. 25, 1982 [CH] Switzerland ............... 3925/82

[51] Int. Cl.$^4$ .................. C07D 317/14; C07D 317/26
[52] U.S. Cl. .................... 549/451; 549/378; 549/377; 549/373; 549/341; 549/333; 549/229; 549/228
[58] Field of Search ............ 549/451, 378, 377, 373, 549/341, 333, 229, 228

[56] References Cited

U.S. PATENT DOCUMENTS 4,202,978  5/1980  Fahrenholtz et al. ............. 544/393
4,473,502  9/1984  Liu et al. ............................ 540/351

*Primary Examiner*—Nicky Chan
*Attorney, Agent, or Firm*—Jon S. Saxe; Bernard S. Leon; Richard J. Mazza

[57] ABSTRACT

There is presented optically uniform β-lactams of the formulae

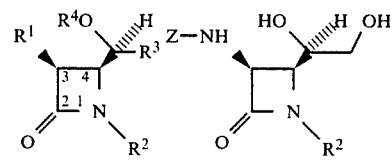

wherein Z is a readily cleavable acyl group, $R^1$ is amino or a group convertible into amino, $R^2$ is hydrogen or a readily cleavable protecting group and $R^3$ and $R^4$ each are a lower hydrocarbon group which optionally contains oxygen and which is attached via a carbon atom, whereby these groups can also be joined with one another to form a ring, with the proviso that $R^1$ is a readily cleavable acylamino when $R^2$ is hydrogen, and the corresponding optical antipodes, their manufacture and use in the manufacture of antimicrobially-active β-lactams as well as novel intermediates usable in their manufacture.

4 Claims, No Drawings

IMINO COMPOUNDS USEFUL FOR MAKING β-LACTAMS

This is a division of application Ser. No. 407,027 filed Aug. 11, 1982, now U.S. Pat. No. 4,576,751.

DESCRIPTION OF THE INVENTION

The present invention is concerned with β-lactams, optically uniform β-lactams of the formula

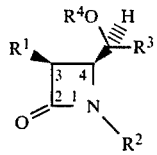

I wherein $R^1$ is amino or a group convertible into amino, $R^2$ is hydrogen or a readily cleavable protecting group and $R^3$ and $R^4$ each are a lower hydrocarbon group which optionally contains oxygen and which is attached via a carbon atom, whereby these groups can also be joined with one another to form a ring, with the proviso that $R^1$ is a readily cleavable acylamino when $R^2$ is hydrogen, and the corresponding optical antipodes.

Objects of the present invention are optically uniform compounds of formula I above and the corresponding antipodes thereof, the manufacture of these compounds and intermediates for the manufacture of these compounds as well as the use of the compounds of formula I in the manufacture of antimicrobially active β-lactams.

The term "lower alkyl" taken alone or in combinations such as in "lower alkoxycarbonyl", "lower alkoxy" and the like denotes straight-chain or branched-chain saturated hydrocarbon groups containing at most 7, preferably at most 4, carbon atoms such as methyl, ethyl, isopropyl and the like.

As groups $R^1$ convertible into amino there come into consideration, for example: azido, phthalimido, (lower alkyl)-OCO—CH=C(CH₃)—NH or readily cleavable acylamino, i.e. Z-NH, in which Z represents a readily cleavable acyl group such as, for example, optionally substituted lower alkoxycarbonyl, such as t-butoxycarbonyl and trichloroethoxycarbonyl; aralykoxycarbonyl such as benzyloxycarbonyl; and benzhydryl.

As readily cleavable protecting groups $R^2$ (denoted by Z' hereinafter) there come into consideration, for example: 2,4- or 3,4-di-(lower alkoxy)-benzyl, especially 2,4- or 3,4-dimethoxybenzyl, 2,4- or 3,4-di-(lower alkoxy)-phenyl, especially 2,4- or 3,4-dimethoxyphenyl, di-[4-(lower alkoxy)-phenyl]-methyl, especially di-(4-methoxyphenyl)-methyl, or 4-(lower alkoxy)-phenyl, especially 4-methoxyphenyl.

Preferred groups

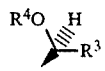

are those in which $R^3$ is lower alkyl, phenyl-lower alkyl, lower alkoxyalkyl, especially lower alkoxymethyl, and $R^4$ is lower alkyl or phenyl-lower alkyl or in which

is a 5- or 6-membered O-heterocycle which optionally contains a further oxygen atom not directly linked with the centre of chirality and which can be substituted, if desired, by lower alkyl, lower alkoxy, oxo or spirocyclo-lower alkyl. Adjacent lower alkoxy groups can together form a ring such as, for example, in the case of isopropylindenedioxy. Especially preferred groups

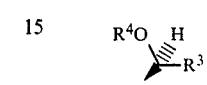

are:

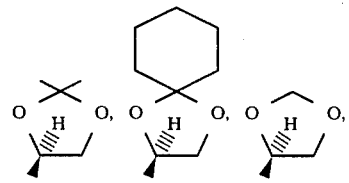

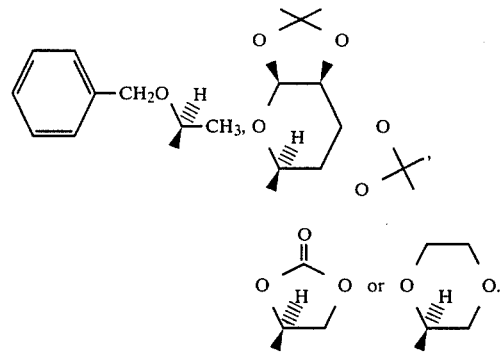

In a special embodiment, the present invention embraces compounds of formula I above in which $R^1$ is phthalimido, amino or benzyloxycarbonylamino, $R^2$ is hydrogen or 2,4-dimethoxybenzyl and

is the group

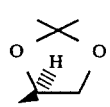

as well as the optical antipodes thereof.

The compounds listed hereinafter are representatives of the class of compound embraced by formula I above:

N-](3S,4S)-Cis-1(2,4-dimethoxybenzyl-4-[(R)-2,2-dimethyl-1,3-dioxolan-4-yl]-2-oxo-3-azetidinyl]phthalimide;

(3S,4S)-cis-3-amino-1-(2,4-dimethoxybenzyl)-4-[(R)-2,2-dimethyl-1,3-dioxolan-4-yl]-2-azetidinone;

benzyl (3S,4S)-cis-1-(2,4-dimethoxybenzyl)-4-](R)-2,2-dimethyl-1,3-dioxolan-4-yl]-2-oxo-3-azetidinecarbamate; and benzyl (3S,4S)-cis-4-[(R)-2,2-dimethyl-1,3-dioxolan-4-yl]-2-oxo-3-azetidinecarbamate.

The β-lactams of formula I and the corresponding optical antipodes thereof can be manufactured in accordance with the invention by reacting a reactive derivative of a carboxylic acid of the formula

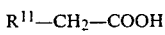

wherein $R^{11}$ is azido, phthalimido or the group RO—CO—CH=C(CH$_3$)—NH— and R is lower alkyl, in the presence of a base with an optically uniform compound of the formula

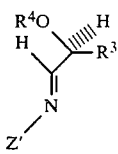

wherein $R^3$ and $R^4$ are as above and $Z'$ is a readily cleavable protecting group, or the optical antipode thereof, if desired, converting the group $R^{11}$ in a thus-obtained compound of the formula

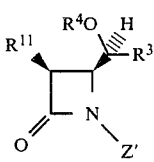

wherein $R^{11}$, $R^3$, $R^4$ and $Z'$ are as above, or in the optical antipode thereof, into the amino group, if desired, reacting a thus-obtained compound of the formula

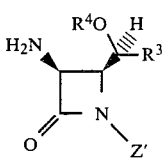

wherein $R^3$, $R^4$ and $Z'$ are as above, or the optical antipode thereof, with an agent yielding the group Z and, if desired, cleaving off the group denoted by Z; in a thus-obtained compound of the formula

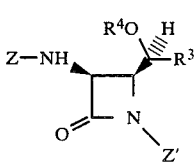

wherein $R^3$, $R^4$, Z and $Z'$ are as above, or in the optical antipode thereof.

The reaction of a reactive derivative of a carboxylic acid of formula II with a compound of formula III or the optical antipode thereof is a cyclo-addition which is familiar to the person skilled in the art. Suitable reactive carboxylic acid derivatives are, for example, the corresponding carboxylic acid halides, especially the carboxylic acid chlorides, the corresponding carboxylic acid anhydrides and mixed anhydrides (e.g. with trifluoroacetic acid, mesitylenesulphonic acid and the like), the corresponding carboxylic acid imidazolides and the like. The reaction is conveniently carried out in the presence of a base, for example a tertiary amine such as triethylamine, and in an inert organic solvent. As solvents in particular ethers come into consideration, such as tetrahydrofuran, diethyl ether, t-butyl methyl ether, dioxan, ethylene glycol dimethyl ether or the like, halogenated hydrocarbons such as methylene chloride, chloroform, 1,2-dichloroethane or the like, acetonitrile, dimethylformamide of the like. The cyclo-addition is carried out in a temperature range of about −30° C. to about 50° C.

The reaction of a compound of formula II with an optically uniform compound of formula III or the optical antipode thereof yields a compound of formula Ia above or the corresponding optical antipode thereof, the substituents in the 3- and 4-position of the azetidine ring being, as expected, cis-positioned to one another. However, it has surprisingly been found that the use of an optically active compound of formula III or of the optical antipode thereof in the foregoing cycloaddition induces two new optical centres of high optical yield, i.e. leads with high diastereo-selectivity to the formation of only one of two possible diastereomeric products. In the product obtained the second possible cis-cycloaddition product, which would be diastereoisomeric to the product actually obtained, could not be detected.

The compounds of formula III or their optical antipodes used as starting materials can be prepared by reacting an aldehyde of the formula

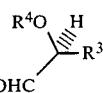

wherein $R^3$ and $R^4$ are as above, or its optical antipode, with an amine of the formula

wherein $Z'$ is as above.

This reaction is preferably carried out in an inert organic solvent, for example in a halogenated hydrocarbon such as methylene chloride, chloroform, 1,2-dichloroethane and the like or in a hydrocarbon such as benzene, toluene and the like. The water which is formed during the reaction is preferably removed continuously, for example by azeotropic distillation or by carrying out the reaction in the presence of a dehydrating agent, for example in the presence of a suitable molecular sieve or of other conventional drying agents such as potassium carbonate, magnesium sulphate and the like. When the water formed during the reaction is removed azeotrophically the reaction is carried out at the boiling point of the chosen solvent; when a dehydrating agent is used the reaction is preferably carried out at room temperature.

The compounds of formula III and their corresponding optical antipodes, which surprisingly yield only the one of two diastereomeric products in the cycloaddition described above, are novel and are likewise an object of the present invention. They need not be isolated, but can be subjected directly to the cycloaddition in accordance with the invention.

The compounds of formula Ib and the optical antipodes thereof can be obtained in accordance with the invention by converting the group $R^{11}$ in a compound of formula Ia or in the optical antipode thereof into the amino group. This conversion can be carried out according to methods which are known per se and which are familiar to any person skilled in the art, the method used depending on the nature of the group $R^{11}$. The phthalimido group can be removed, for example, by reaction with hydrazine, methylhydrazine or the like, conveniently in an inert organic solvent. Suitable solvents are, for example, halogenated hydrocarbons such as methylene chloride, chloroform and the like, ethers such as tetrahydrofuran, dioxan, t-butyl methyl ether and the like, etc. The azido group can be reduced to the amino group, for example, with elemental hydrogen in the presence of a catalyst such as palladium/carbon, Raney-nickel, platinium oxide and the like. The group ROCO—CH=C(CH$_3$)—NH— can be converted into the amino group, for example, by mild acidic hydrolysis.

By reacting a compound of formula Ib or the optical antipode thereof with an agent yielding the group Z there is obtained in accordance with the invention a compound of formula Ic or the optical antipode thereof. Suitable agents yielding the group Z are, for example, di-t-butyl dicarbonate or chloroformic acid esters such as benzyl chloroformate, t-butyl chloroformate, 2,2,2-trichloroethyl chloroformate and the like. The reaction is conveniently carried out in an inert organic solvent, for example in a halogenated hydrocarbon such as methylene chloride, chloroform and the like, and conveniently in the presence of an acid-binding agent such as butylene oxide, triethylamine, quinuclidine etc. The reaction is conveniently carried out at room temperature.

By cleavage of the group denoted by Z' from a compound of formula Ic or from the optical antipode thereof there is obtained a compound of the formula

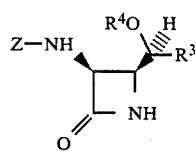

Id wherein $R^3$, $R^4$ and Z are as above,
or the corresponding optical antipode thereof.

The cleavage of the group denoted by Z' from a compound of formula Ic or from the optical antipode thereof is conveniently carried out by mild oxidation. A suitable oxidizing agent is cerium ammonium nitrate (e.g. in aqueous acetonitrile or in aqueous acetone). 2,4- and 3,4-di-(lower alkoxy)-benzyl and di-[4-(lower alkoxy)-phenyl]-methyl groups can be cleaved off with a buffered peroxodisulphate (e.g. ammonium peroxodisulphate/ammonia or potassium peroxodisulphate/dipotassium hydrogen phosphate), the cleavage being carried out in water and under approximately neutral conditions. Di-4-(lower alkoxy)-phenyl-methyl groups can be cleaved off acidolytically, for example by the action of trifluoroacetic acid, formic acid or aluminium chloride in an inert organic solvent such as methylene chloride or anisole.

The compounds of formula I and the corresponding optical antipodes thereof are valuable intermediate products for the manufacture of pharmaceutically active substances. In particular, they can be used for the manufacture of antibiotically active isocephalosporins. Such isocephalosporins and their manufacture from compounds of the formula

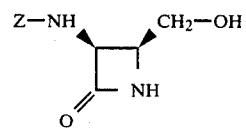

VI wherein Z is as above,
are described in detail in German Offenlegungsschrift No. 2 619 458.

The compounds of formula VI and the corresponding optical antipodes thereof can be prepared, for example, by cleaving the hydrocarbon group $R^5$ in a compound of the formula

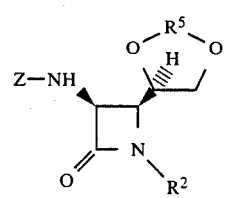

Id$^1$ wherein $R^5$ is a hydrocarbon group (e.g. methylene, ethylene, oxomethylene, cyclohexylidene or, preferably, isopropylidene) and Z and $R^2$ are as above,
or in the optical antipode thereof, the cleavage being carried out, for example, by treatment with a mild acidic agent such as, for example, with a sulphonated ion exchanger, pyridinium p-toluenesulphonate or p-toluenesulphonic acid in a lower alkanol such as methanol or ethanol or in aqueous tetrahydrofuran, preferably at room temperature to about 80° C. There is obtained an optically active diol of the formula

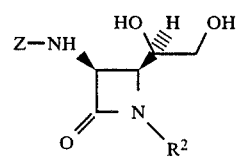

VII wherein Z and $R^2$ are as above,
or the optical antipode thereof.

The diol grouping in the thus-obtained compound of formula VII or in the optical antipode thereof is cleaved, there being obtained an aldehyde of the formula

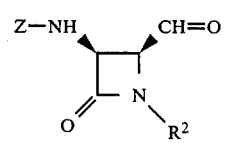

VIII wherein Z and $R^2$ are as above, or the optical antipode thereof. This cleavage is carried out according to methods known per se and can be accomplished, for example, with an alkali metal periodate such as sodium metaperiodate in water, optionally in admixture with, for example, tetrahydrofuran or a lower alkanol such as methanol. For the conversion into the alcohol of formula VI or into the optical antipode thereof, the aldehyde group of the aldehyde of formula VIII or of the optical antipode thereof is reduced according to known methods, for example by treatment with a complex metal hydride such as sodium borohydride in a lower alkanol such as ethanol, isopropanol or the like. A resulting alcohol of the formula

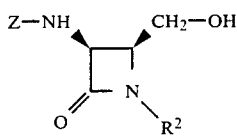

VIa wherein Z and $R^2$ are as above,
or the optical antipode thereof can, insofar as $R^2$ is a readily cleavable group Z', be converted in the above manner by mild oxidation into the desired alcohol of formula VI which is not protected at the nitrogen or into the optical antipode thereof.

Compounds of the formula

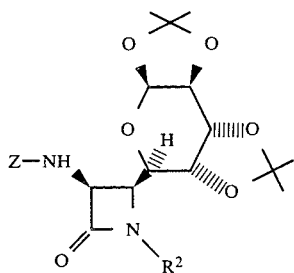

$Id^2$ wherein $R^2$ and Z are as above,
or the optical antipodes thereof can be converted into the aldehydes of formula VIII or into the optical antipodes thereof by acidic hydrolysis, for example with a mineral acid in a lower alkanol (such as hydrochloric acid in methanol) and subsequent reaction with aqueous sodium metaperiodate.

Benzyloxy groups present such as, for example, in compounds of the formula

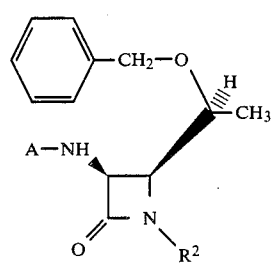

$Id^3$ wherein Z and $R^2$ are as above,
or in the optical antipodes thereof can be cleaved off hydrogenolytically and the resulting corresponding carbinol of the formula

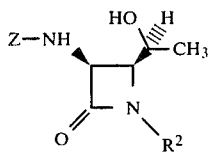

VIIa wherein Z and $R^2$ are as above,
or the optical antipode thereof can be reacted further (e.g. in analogy to compound 9 in Scheme II hereinafter).

The compounds of formula I or the optical antipodes thereof can be converted into optically uniform α-lactams having antimicrobial properties by introducing suitable groups in positions 1, 3 and 4. The substituent in position 4 can be functionally modified, for example by transformation of the above-described 4-formyl or 4-hydroxymethyl groups in a manner which is known to the person skilled in the art. After removing a protecting group $R^2$ which may be present, the group $-SO_3H$ can be introduced in position 1 by reaction with a reactive derivative of sulphur trioxide, for example by reaction with complexes of sulphur trioxide and a base such as pyridine, trimethylamine, picoline etc at about 0°-80° C. in an inert organic solvent, for example in an ether such as dioxan, in pyridine, in dimethylformamide etc. In position 3, the amino group $R^1$ can be liberated, prior to or after the last-mentioned reaction, by cleavage of the protecting group; for example, aralkoxycarbonyl groups (especially benzyloxycarbonyl) or the benzhydryl group can be cleaved off hydrogenolytically (e.g. by the action of hydrogen and palladium/carbon), the t-butoxycarbonyl group can be cleaved off by treatment with trifluoroacetic acid or formic acid and the trichloroethoxycarbonyl group can be cleaved off by treatment with zinc and a protonic acid such as acetic acid or hydrochloric acid. Subsequently, the liberated amino group $R^1$ can be acylated with a corresponding substituted carboxylic acid or a reactive functional derivative thereof, for example acid anhydride, acid amide, activated ester (e.g. a thioester such as the benzthiazolyl thioester, whereby the widest variety of acyl groups as are known, for example, from penicillin or cephalosporin chemistry can be introduced. For example, in this manner there can be manufactured according to methods known per se optically uniform, antimicrobially active β-lactams of the formula

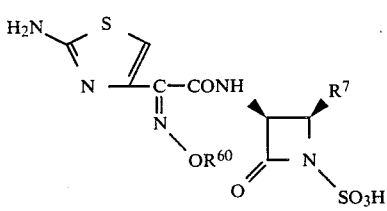

IX wherein $R^{60}$ is hydrogen, lower alkyl or carboxy-lower alkyl and $R^7$ is a lower organic group (e.g. carbamoyl or carbamoyloxymethyl),
or the corresponding optical antipodes thereof.

Examples of corresponding conversions into end products are illustrated in the following Reaction Schemes I–III.

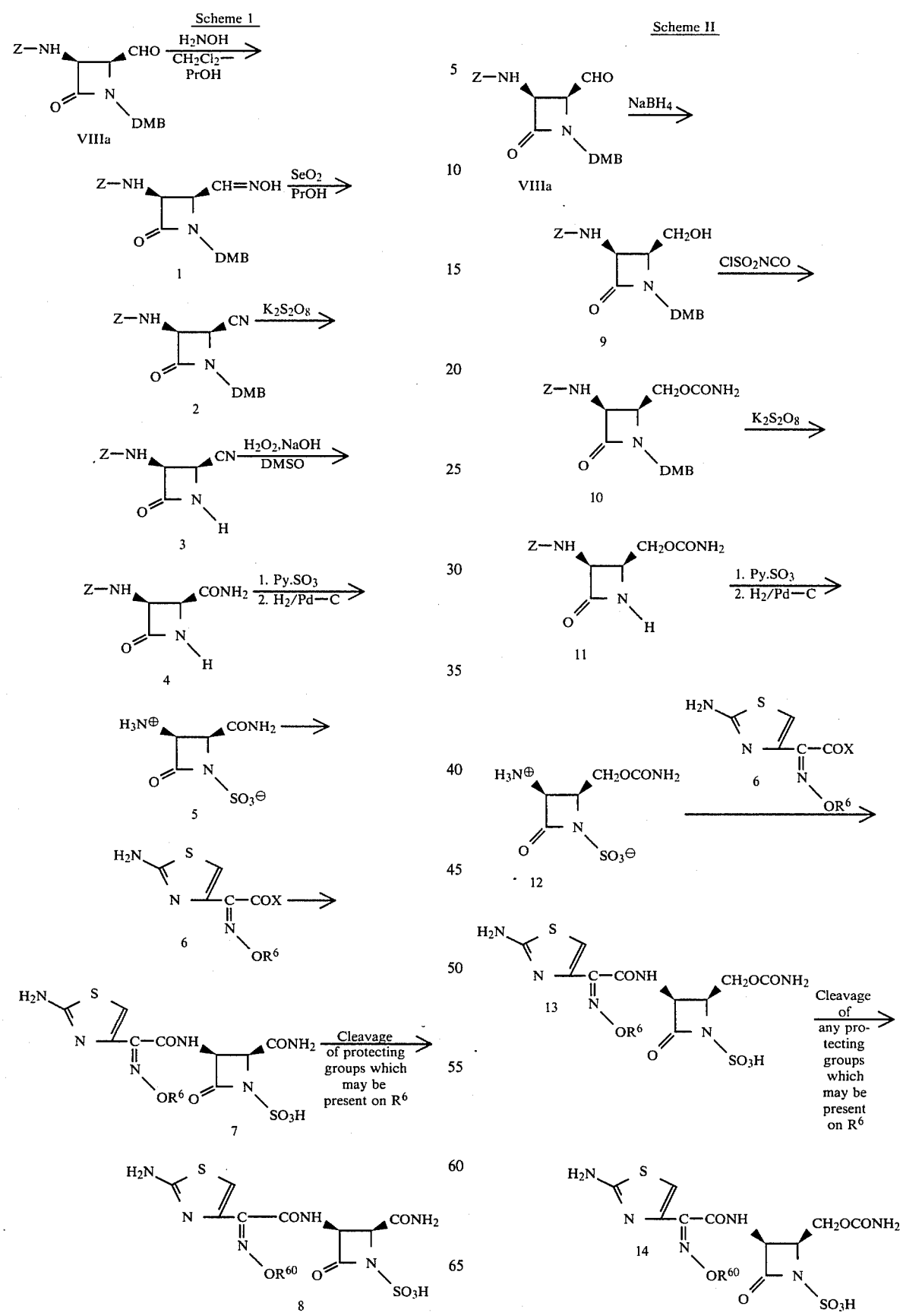

Scheme III

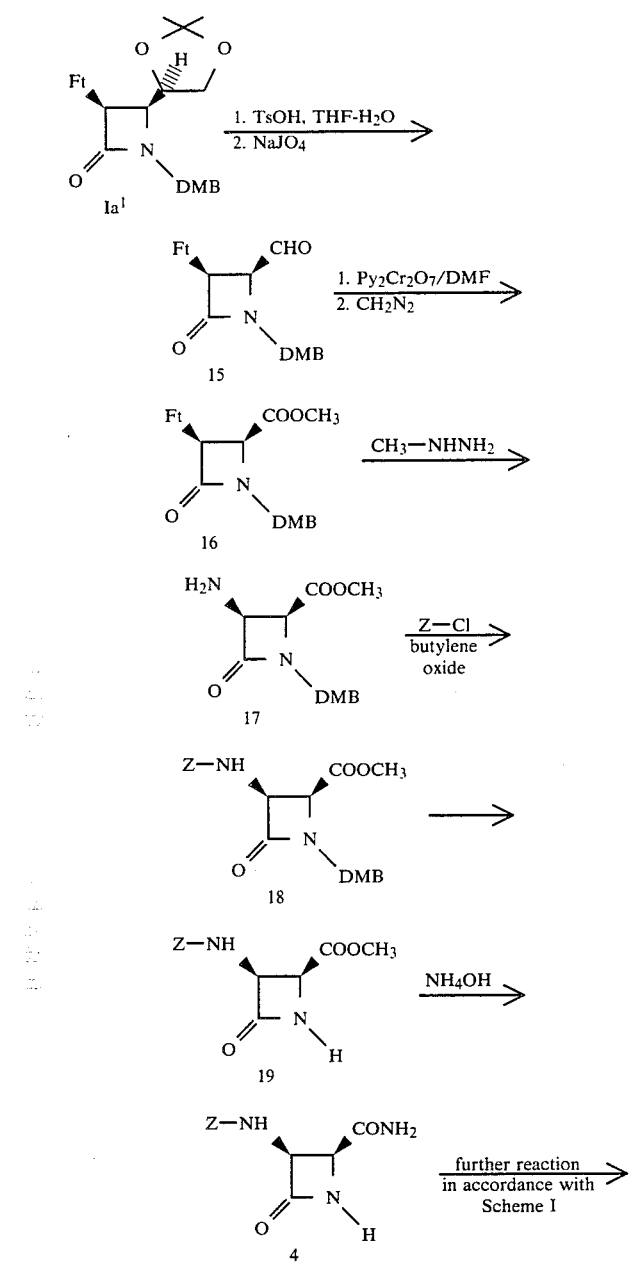

Explanation of the symbols and abbreviations used in Schemes I, II and III

DMB = 2,4-dimethoxybenzyl (can be replaced by other protecting groups Z')
DMF = dimethylformamide
PrOH = n-propanol
DMSO = dimethyl sulphoxide
Py = pyridine
Py.SO$_3$ = sulphur trioxide/pyridinium complex
COX = reactive derivative of a carboxylic acid [e.g. acid anhydride, acid amide, activated ester (e.g. benzthiazolyl ester)]
R$^6$ = hydrogen, lower alkyl (e.g. methyl), protected carboxy-lower alkyl (e.g. protected carboxy-methyl, protected 1-methyl-1-carboxy-ethyl). Protecting group: e.g. t-butyl (cleavable with e.g. trifluoroacetic acid), benzyl and p-nitrobenzyl (cleavable with e.g. hydrogen and palladium/carbon), 2-(trimethylsilyl)-ethyl (cleavable with e.g. tetrabutylammonium fluoride)
R$^{60}$ = hydrogen, lower alkyl (e.g. methyl), carboxy-lower alkyl (e.g. carboxymethyl, 1-methyl-1-carboxy-ethyl).

The following Examples illustrate the present invention in more detail, but are not intended to limit its scope in any manner. All temperatures are given in degrees Centigrade. The optical rotation [α]$_D$ was measured at 20° C.

Abbreviations used in the analytical data:
Ft = phthalimido;
Ar = aromatic;
Me = methyl;
φ = phenyl;
Bz = benzyl.

EXAMPLE 1

To a solution, stirred at room temperature, of 4.9 g (37.65 mmol) of isopropylidene-D-glyceraldehyde in 100 ml of dry methylene chloride (methanol-free) are added to 10 g of molecular sieve 4Å and subsequently dropwise a solution of 6.29 g (37.65 mmol) of 2,4-dimethoxybenzylamine in 20 ml of dry methylene chloride. The mixture is stirred at room temperature for 2 hours, subsequently treated with 5 g of anhydrous magnesium sulphate, stirred for a further 30 minutes and subsequently filtered, the filter cake being washed with 20 ml of methylene chloride.

The resulting organic solution of isopropylidene-D-glyceraldehyde (2,4-dimethoxybenzyl)imine is cooled to −18° under argon and treated while stirred with 5.5 ml (39.5 mmol) of triethylamine. After a few minutes there is added thereto over a period of 1 hour a solution of 8.8 g (39.3 mmol) of phthaloylglycyl chloride in 100 ml of dry methylene chloride, the mixture is stirred at −15° for 2 hours and subsequently left to warm to room temperature. The mixture is stirred at room temperature overnight, washed three times with 100 ml of water each time and with 100 ml of sodium chloride solution and the solution obtained is dried over sodium sulphate. The solution is evaporated and the residue obtained is chromatographed on a silica gel column (granular size: 230–400 mesh) while eluting with hexane/ethyl acetate (1:1). There are obtained 15.8 g (90%) of N-[(3R,4R)-cis-1-(2,4-dimethoxybenzyl)-4-[(S)-2,2-dimethyl-1,3-dioxolan-4-yl]-2-oxo-3-azetidinyl]phthalimide as a foam; [α]$_D$ = −37° (c=1 in chloroform); MS: 466 (M+). After recrystalization from ethyl acetate, there are obtained colourless crystals of melting point 155°; [α]$_D$ = −49.2° (c=0.8 in chloroform).

EXAMPLE 2

A solution of 9.7 g (20.8 mmol) of N-[(3R,4R)-cis-1-(2,4-dimethoxybenzyl)-4-[(S)-2,2-dimethyl-1,3-dioxolan-4-yl]-2-oxo-3-azetidinyl]phthalimide in 120 ml of methylene chloride is treated with 2.17 ml (40.8 mmol) of methylhydrazine. The mixture is stirred at 28° overnight, precipitated material is filtered off and the filtrate is evaporated under reduced pressure. The residue is taken up in 70 ml of ethyl acetate and the suspension obtained is filtered. The filtrate is washed three times with 100 ml of water each time and with 150 ml of sodium chloride solution and dried over sodium sulphate. After evaporation of the solvent, there are obtained 5.2 g (74%) of crude (3R,4R)-cis-3-amino-1-(2,4-dimethoxybenzyl)-4-[(S)-2,2-dimethyl-1,3-dioxolan-4-yl]-2-azetidinone which is used in the next step without further purification.

EXAMPLE 3

A stirred solution of 5.2 g (15.47 mmol) of (3R,4R)-cis-3-amino-1-(2,4-dimethoxybenzyl)-4-[(S)-2,2-dimethyl-1,3-dioxolan-4-yl-2-azetidinone and 4.8 ml (62 mmol) of butylene oxide in 120 ml of methylene chloride is treated dropwise with 2.8 ml (20 mmol) of carbobenzoxy chloride, the mixture is stirred for 1 hour and subsequently evaporated under reduced pressure. The crude material obtained is treated with dry ether, there being obtained a crystalline material which is chromatographed on a silica gel column (granular size: 230–400 mesh) while eluting with hexane/ethyl acetate (1:1). There are obtained 6.53 g (90%) of benzyl (3R,4R)-cis-1-(2,4-dimethoxybenzyl)-4-[(S)-2,2-dimethyl-1,3-dioxolan-4-yl]-2-oxo-3-axetidine-carbamate of melting point 115°–116°; $[\alpha]_D = -46°$ (c=0.3 in methanol).

EXAMPLE 4

A stirred solution of 6.53 g (13.87 mmol) of benzyl (3R,4R)-cis-1-(2,4-dimethoxybenzyl)-4-[(S)-2,2-dimethyl-1,3-dioxolan-4-yl]-2-oxo-3-azetidinecarbamate in 450 ml of acetonitrile is treated dropwise at 90° and under argon with a solution of 6.0 g (22.2 mmol) of potassium persulphate and 3.75 g (21.55 mmol) of dipotassium hydrogen phosphate in 150 ml of water. The mixture is stirred for 2 hours, left to cool and the pH is adjusted to 6–7 by adding excess dipotassium hydrogen phosphate (about 6 g). The mixture is filtered and the filtrate is evaporated under reduced pressure. The residue is taken up in 200 ml of methylene chloride, washed four times with 70 ml of water each time and with 70 ml of sodium chloride solution. After drying and evaporation, the oily residue is chromatographed on a silica gel column (granular size: 230–400 mesh) while eluting with ethyl acetate/n-hexane (7:3). There are obtained 2.52 g (56.7%) of benzyl (3R,4R)-cis-4-[(S)-2,2-dimethyl-1,3-dioxolan-4-yl]-2-oxo-3-azetidinecarbamate of melting point 140°–141°; $[\alpha]_D = 46°$ (c=0.5 in methanol). The absolute configuration of this compound was confirmed by X-ray structure analysis.

EXAMPLE 5

A solution of 320 mg (0.68 mmol) of benzyl (3R,4R)-cis-1-(2,4-dimethoxybenzyl)-4-[(S)-2,2-dimethyl-1,3-dioxolan-4-yl]-2-oxo-3-azetidinecarbamate in 40 ml of methanol is stirred overnight in the presence of 4 g of Amberlite IR 120 (H+ form). The mixture is filtered, the polymeric material being carefully washed twice with 20 ml of methanol each time. The combined filtrates are evaporated and there are obtained 272 mg (97.2%) of pure benzyl (3R,4R)-cis-4-[(S)-1,2-dihydroxyethyl]-1-(2,4-dimethoxybenzyl-2-oxo-3-azetidinecarbamate.

EXAMPLE 6

A solution of 90 mg (0.21 mmol) of benzyl (3R,4R)-cis-4-[(S)-1,2-dihydroxyethyl]-1-(2,4-dimethoxybenzyl)-2-oxo-3-azetidinecarbamate in 18 ml of methanol is treated dropwise while stirring with a solution of 60 mg (0.28 mmol) of sodium metaperiodate in 2 ml of water. The mixture is stirred for 1 hour, filtered and the filtrate is evaporated under reduced pressure. The residue is taken up in 20 ml of ethyl acetate and washed twice with 10 ml of water each time and with 10 ml of sodium chloride solution. After drying and evaporation, there are obtained 66 mg (76%) of pure benzyl (3R,4R)-cis-1-(2,4-dimethoxybenzyl)-4-formyl- 2-oxo-3-azetidinecarbamate of melting point 147°–149° (from ethyl acetate/hexane); $[\alpha]_D = -32°$ (c=0.2 in methanol).

EXAMPLE 7

(a) To a solution, stirred for room temperture, of 0.9 g (5.4 mmol) of 2,4-dimethoxybenzylamine in 100 ml of methylene chloride are added 3 g of molecular sieve 4Å and after 20 minutes 0.7 (5.4 mmol) of isopropylidene-L-glyceraldehyde and 5 g of anhydrous magnesium sulphate. The mixture is subsequently stirred at room temperature for a further 1 hour. The resulting organic solution of isopropylidene-L-glyceraldehyde (2,4-dimethoxybenzyl)imine is cooled to −20° under argon and treated while stirring with 0.88 ml (5.4 mmol) of triethylamine. Then, a solution of 1.25 g (5.6 mmol) of phthaloylglycyl chloride in 20 ml of dry methylene chloride is added dropwise within 1 hour and the mixture is subsequently stirred at room temperature overnight. The mixture is worked-up as described in Example 1 and there are obtained after chromatography 1.77 g (70%) of N-[(3S,4S)-cis-1-(2,4-dimethoxybenzyl)-4-[(R)-2,2-dimethyl-1,3-dimethyl-1,3-dioxolan-4-yl]-2-oxo-3-azetidinyl]phthalimide as a foam; $[\alpha]_D = -41°$ (c=0.8 in chloroform); MS: 466 (M+). After recrystallization from ethyl acetate, there is obtained a crystalline product with $[\alpha]_D = -48°$ (c=0.6 in chloroform).

(b) From 1.6 g (3.4 mmol) of N-[(3S,4S)-cis-1-(2,4-dimethoxybenzyl)-4-[(R)-2,2-dimethyl-1,3-dioxolan-4-yl]-2-oxo-3-azetidinyl]phthalimide there is obtained in analogy to the details in Example 2 1.0 g (87%) of crude (3S,4S)-cis-3-amino-1-(2,4-dimethoxybenzyl)-4-[(R)-2,2-dimethyl-1,3-dioxolan-4-yl-2-azetidinone.

(c) From 1.0 g (3.0 mmol) of (3S,4S)-cis-3-amino-1-(2,4-dimethoxybenzyl)-4-[(R)-2,2-dimethyl-1,3-dioxolan-4-yl]-2-azetidinone there are obtained in analogy to the details in Example 3 1.2 g (85%) of benzyl (3S,4S)-cis-1-(2,4-dimethoxybenzyl)-4-[(R)-2,2-dimethyl-1,3-dioxolan-4-yl]-2-oxo-3-azetidinecarbamate of melting point 115°–117°.

(d) From benzyl (3S,4S)-cis-1-(2,4-dimethoxybenzyl)-4-[(R)-2,2-dimethyl-1,3-dioxolan-4-yl]-2-oxo-3-azetidinecarbamate there can be prepared in analogy to the details in Example 4 benzyl (3S,4S)-cis-4-[(R)-2,2-dimethyl-1,3-dioxolan-4-yl]-2-oxo-3-azetidinecarbamate.

(e) Benzyl (3S,4S)-cis-1-(2,4-dimethoxybenzyl)-4-[(R)-2,2-dimethyl-1,3-dioxolan-4-yl]-2-oxo-3-azetidinecarbamate can be converted in analogy to the details in Example 5 into benzyl (3S,4S)-cis-4-[(R)-1,2-dihydroxyethyl]-1-(2,4-dimethoxybenzyl)-2-oxo-3-azetidinecarbamate.

(f) From benzyl (3S,4S)-cis-4-[(R)-1,2-dihydroxyethyl]-1-(2,4-dimethoxybenzyl)-2-oxo-3-azetidinecarbamate there can be obtained in analogy to the details in Example 6 benzyl (3S,4S)-cis-1-(2,4-dimethoxybenzyl)-4-formyl-2-oxo-3-azetidinecarbamate.

EXAMPLE 8

(a) 7.0 g (0.015 mol) of benzyl (3S,4S)-cis-1-(2,4-dimethoxybenzyl)-4-[(R)-2,2-dimethyl-1,3-dioxolan-4-yl]-2-oxo-3-azetidinecarbamate are dissolved in 100 ml of acetonitrile. This solution is added dropwise to a solution, heated to 98°, of 6.5 g (0.024 mol) of potassium peroxodisulphate and 4.2 g (0.024 mol) of dipotassium hydrogen phosphate. During the addition of pH value is held at 6 by adding a further 10 g of dipotassium hydrogen phosphate. The mixture is stirred for 14 hours, subsequently cooled, filtered and partially evaporated. The aqueous phase is subsequently extracted with ethyl acetate. The organic phase is washed successively with water and aqueous sodium chloride solution, dried over sodium sulphate, filtered and evaporated. The oil obtained is chromatographed on silica gel [230–400 mesh, n-hexane/ethyl acetate (1:1) as the elution agent]. There are obtained 3.9 g (82%) of benzyl (3S,4S)-cis-4-[(R)-2,2-dimethyl-1,3-dioxolan-4-yl]-2-oxo-3-azetidinecarbamate as colourless crystals of melting point 142°. MS: 305 (M-CH$_3$); $[\alpha]_D = +57°$ (c=0.5 in methanol).

(b) 350 mg (1.09 mmol) of benzyl (3S,4S)-cis-4-[(R)-2,2-dimethyl-1,3-dioxolan-4-yl]-2-oxo-3-azetidinecarbamate are dissolved in 25 ml of methanol and stirred at room temperature for 12 hours in the presence of 10 g of Amberlite IR 120 (H+form; pre-washed with methanol). The mixture is subsequently filtered and treated dropwise with a solution of 232 mg (1.08 mmol) of sodium metaperiodate. After stirring for 2 hours, the mixture is partially evaporated and extracted with ethyl acetate. The organic phase is washed successively with water and aqueous sodium chloride solution, dried over sodium sulphate, filtered and evaporated. There are obtained 250 mg (92%) of benzyl (3S,4S)-cis-4-formyl-2-oxo-3-azetidinecarbamate. MS: 248 (M+).

EXAMPLE 9

1 g (3.87 mmol) of (1,2:3,4)-di-0-isopropylidene-α-D-galacto-hexodialdo-1,5-pyranose are dissolved in 60 ml of absolute methylene chloride, containing 5 g of molecular sieve 4Å, while stirring in an argon atmosphere. The solution is treated dropwise at room temperature with a solution of 0.68 g (4 mmol) of 2,4-dimethoxybenzylamine in 10 ml of methylene chloride. The solution is stirred at room temperature for 30 minutes, subsequently cooled to −20° and treated with 0.65 ml (0.47 g, 4.6 mmol) of triethylamine and after a few minutes with a solution of 0.8 g (0.40 mmol) of phthaloylglycyl chloride in 20 ml of methylene chloride. The mixture is warmed to room temperature and subsequently stirred for 1.5 hours. After filtration, the organic solution obtained is washed twice with 150 ml of water each time and once with 10 ml of aqueous sodium chloride solution and then dried over magnesium sulphate. After evaporation of the solvent and chromatographic purification on silica gel [230–400 mesh; n-hexane/ethyl acetate (1:1) as the solvent], there are obtained 1.8 g (75%) of N-[cis-1-(2,4-dimethoxybenzyl)-2-oxo-4-[(3aαH,-8bαH)-tetrahydro-2,2,7,7-tetramethyl-5H-bis[1,3]dioxolo [4,5-b:4',5'-d]pyran-5-yl-3-azetidinyl-phthalimide as a foam; $[\alpha]_D = -27°$ (c=1% in methanol); MS: 594 (M+); IR: 1767, 1722 cm$^{-1}$ (KBr).

EXAMPLE 10

2.0 g (11.76 mmol) of cyclohexylidene-D-glyceraldehyde are dissolved in 8 ml of absolute methylene chloride and treated at room temperature with 2.06 g (12.35 mmol) of 2,4-dimethoxybenzylamine. After stirring for 30 minutes, the mixture is cooled to 0° and treated with 1.96 ml (14.11 mmol) of triethylamine and dropwise with a solution of 2.76 g (12.35 mmol) of phthaloylglycyl chloride in 4 ml of methylene chloride. The mixture is stirred at room temperature for 12 hours, subsequently diluted with 100 ml of methylene chloride, washed in succession with 30 ml of water, 30 ml of 0.1N aqueous hydrochloric acid, 30 ml of water and 30 ml of aqueous sodium chloride solution and dried over sodium sulphate. The solvent is removed by evaporation and the residue is purified by chromatography on silica gel [230–400 mesh; ethyl acetate/n-hexane (1:1) as the solvent). There are obtained 4.3 g (72%) of N-[(3R,4R)-1-(2,4-dimethoxybenzyl)-4-[(S)-1,4-dioxaspiro[4.5]dec-2-yl]-2-oxo-3-azetidinyl]phthalimide; $[\alpha]_D = -18°$ (c=0.5 in methanol).

Elemental analysis for $C_{28}H_{30}N_2O_7$: Calculated: C 66.39, H 5.97, N 5.53%. Found: C 65.94, H 5.94, N 5.57%.

IR (KBr) cm$^{-1}$: 3435, 1768, 1721, 1589, 1508, 1208.

NMR (CDCl$_3$) δ(ppm): 1.2–1.6 (10H, m, (CH$_2$)$_5$), 3.35 (1H, dd, 6 and 9 Hz, H-4), 3.5–3.8 (2, m, O—CH$_2$) 3.81 and 3.82 (6H, 2s, 2 x OCH$_3$), 4.20 (1H, m, O—CH), 4.15 and 4.90 (2H, 2d, 14 Hz, N—CH$_2$—Ar), 5.25 (1H, d, 6 Hz, H$_3$), 6.50 (2H, m, 2H Ar), 7.27 (1H, d, Ar), 7.85 (4H, m, Ar).

MS: M+: 506

EXAMPLE 11

To a solution, stirred at room temperature, of 0.9 g (5.4 mmol) of 3,4-dimethoxybenzylamine in 100 ml of methylene chloride are added 3 g of molecular sieve 4 Å and after 20 minutes 0.7 g (5.4 mmol) of isopropylidene-L-gylceraldehyde and 5 g of anhydrous magnesium sulphate. The mixture is subsequently stirred at room temperature for 1 hour. The resulting organic solution of isopropylidene-L-glyceraldehyde (3,4-dimethoxybenzyl)imine is cooled to −20° under argon and treated while stirring with 0.88 ml (5.4 mmol) of triethylamine. Then, a solution of 1.25 g (5.6 mmol) of phthaloylglycyl chloride in 20 ml of dry methylene chloride is added dropwise thereto within 1 hour and the mixture is subsequently stirred overnight at room temperature. The mixture is worked-up as described in Example 1 and there are obtained after chromatography 1.56 g (62%) of N-(3S,4S)-cis-1-(3,4-dimethoxybenzyl)-4-[(R)-2,2-dimethyl-1,3-dioxolan-4-yl]-2-oxo-3-azetidinyl]phthalimide as a foam; $[\alpha]_D = +16.2°$ (c=1.0 in methanol); MS: 466 (M+).

Elemental analysis for $C_{25}H_{26}N_2O_7$: Calculated: C 64.37, H 5.62, N 6.01%. Found: C 63.53, H 5.72, N 5.96%.

IR (KBr cm$^{-1}$): 3430, 1766, 1721, 1609, 1517.

EXAMPLE 12

To a solution, stirred at room temperature, of 670 mg (4 mmol) of 3,4-dimethoxybenzylamine in 70 ml of methylene chloride are added 2.5 g of molecular sieve 4 Å and after 20 minutes 660 mg (4 mmol) of (S)-2-benzyloxypropionaldehyde and 3.7 g of anhydrous magnesium sulphate. The mixture is subsequently stirred at room temperature for 1 hour. The resulting solution is cooled to −20° in an argon atmosphere and treated while stirring with 0.65 ml (4 mmol) of triethylamine. Then, a solution of 930 mg (4.15 mmol) of phthaloylglycyl chloride is added dropwise thereto within 1 hour and the mixture is subsequently stirred at room temperature for 12 hours. The mixture is worked-up as described in Example 1 and there are obtained after chromatography 990 mg (50%) of N-[(3S,4S)-4-[(S)-1-(benzyloxy)ethyl]-1-(2,4-dimethylbenzyl)-2-oxo-3-azetidinyl]phthalimide as a foam; $[\alpha]_D = +44.6°$ (c=1 in chloroform); MS: =500 (M+).

Elemental analysis for $C_{29}H_{28}N_2O_6$: Calculated: C 69.59, H 5.64, N 5.60%. Found: C 69.06, H 5.80, N 5.36%.

IR (KBr) $cm^{-1}$: 1766, 1721, 1613, 1589, 1508.

EXAMPLE 13

20.8 g (44.59 mmol) of N-[(3S,4S)-cis-1-(2,4-dimethoxybenzyl)-4-[(R)-2,2-dimethyl-1,3-dioxolan-4-yl]-2-oxo-3-azetidinyl]phthalimide are dissolved in 300 ml of tetrahydrofuran/water (2:1) and treated with 1.5 g (7.88 mmol) of p-toluenesulphonic acid monohydrate. The mixture is heated gently under reflux conditions for 48 hours and subsequently cooled. The pH value is adjusted to 7 by adding saturated aqueous sodium bicarbonate solution and the solution obtained is treated while stirring with an aqueous solution of 10.5 g (49.11 mmol) of sodium metaperiodate. After 1 hour, the mixture is filtered and the mother liquor is partially evaporated under reduced pressure. The aqueous solution obtained is extracted twice with 200 ml of ethyl acetate. The organic phase is washed successively with 200 ml of water and 150 ml of aqueous sodium chloride solution and dried over sodium sulphate. After evaporation and purification by chromatography [230–400 mesh; ethyl acetate/n-hexane (7:3) as the eluting agent], there is obtained N-[(3S,4S)-cis-1-(2,4-dimethoxybenzyl)-4-formyl-2-oxo-3-azetidinyl]phthalimide in a yield of 15.96 g (90.8%).

NMR (CDCl$_3$) δ(ppm): 3.80 (6H, s, 2×OCH$_3$), 4.10 (1H, dd, 3 and 5 Hz, CH—CHO), 4.55 (2H, s, N—CH$_2$), 5.50 (1H, d, 5 Hz, Ft—CH), 6.40 (2H, m, Ar), 7.20 (1H, m, Ar), 7.70 (4H, s, Ar), 9.50 (1H, d, 3 Hz, CHO).

EXAMPLE 14

(a) 9.8 g (26 mmol) of pyridinium dichromate are dissolved in 20 ml of absolute dimethylformamide and treated at room temperature with a solution of 5.1 g (13 mmol) of N-[(3S,4S)-cis-1-(2,4-dimethoxybenzyl)-4-formyl-2-oxo-3-azetidinyl]phthalimide in 20 ml of absolute dimethylformamide. The mixture is stirred at room temperature for 12 hours and subsequently poured into ice/water. The mixture is extracted twice with 100 ml of ethyl acetate each time. The combined organic phases are washed successively twice with 100 ml of water and twice with 100 ml of aqueous sodium chloride solution and then dried over sodium sulphate. After evaporation of the solvent, there are obtained 2.5 g (48%) of (3S,4S)-cis-1-(2,4-dimethoxybenzyl)-3-phthalimido-2-azetidinone-4-carboxylic acid as a foam. MS: 410 (M+), 263.

IR (KBr, $cm^{-1}$): 2500, 1767, 1724, 1612, 1509.

NMR (d$_6$-DMSO) δ(ppm): 4.85 (6H, s, 2×OCH$_3$), 4.20 (1H, d, 5.5 Hz, CH—COOH), 4.40 and 4.90 (2H, 2d, 14 Hz, N—CH$_2$), 5.55 (1H, d, 5.5 Hz, Ft—CH), 6.50 (2H, m, Ar), 7.30 (1H, m, Ar), 7.80 (4H, m, Ar).

(b) A suspension of 250 mg (0.61 mmol) of (3S,4S)-cis-1-(2,4-dimethoxybenzyl)-3-phthalimido-2-azetidinone-4-carboxylic acid in absolute ether is treated with 20 ml of an ethereal solution of diazomethane until the evolution of nitrogen gas has faded away. The mixture is evaporated and the residue is chromatographed on silica gel [230–400 mesh, ethyl acetate/n-hexane (1:1) as the eluting agent]. There are obtained 200 mg (77%) of (3S,4S)-cis-1-(2,4-dimethoxybenzyl)-3-phthalimido-2-azetidinone-4-carboxylic acid methyl ester.

NMR (CDCl$_3$) δ(ppm): 3.63 (3H, s, COOCH$_3$), 3.81 (6H, s, 2×OMe), 4.20 (1H, d, 5.5 Hz, CHCOOMe), 4,40 and 4.90 (2H, 2d, 14 Hz, N—CH$_2$), 5.49 (1H, d, 5.5 Hz, Ft—CH), 6.50 (2H, m, Ar), 7.20 (1H, m, Ar), 7.90 (4H, m, Ar).

EXAMPLE 15

(a) To a solution, stirred at room temperature, of 0.9 g (5.4 mmol) of 2,4-dimethoxybenzylamine in 100 ml of methylene chloride are added 3 g of molecular sieve 4 Å and after 20 minutes 0.7 g (5.4 mmol) of isopropylidene-L-glyceraldehyde and 5 g of anhydrous magnesium sulphate. The mixture is subsequently stirred at room temperature for 1 hour. The resulting organic solution of isopropylidene-L-glyceraldehyde (2,4-dimethoxybenzyl)imine is cooled to −20° under argon and treated while stirring with 0.88 ml (5.4 mmol) of triethylamine. Then, a solution of 1.25 g (5.6 mmol) of phthaloylglycyl chloride in 20 ml of dry methylene chloride is added dropwise thereto within 1 hour and subsequently the mixture is stirred at room temperature overnight. The mixture is washed three times with 100 ml of water each time and with 100 ml of sodium chloride solution and dried over sodium sulphate. The solution is evaporated and the residue is chromatographed on silica gel (230–400 mesh) while eluting with hexane/ethyl acetate (1:1). There are obtained 1.77 g (70%) of N-[(3S,4S)-cis-1-(2,4-dimethoxybenzyl)-4-[(R)-2,2-dimethyl-1,3-dioxolan-4-yl]-2-oxo-3-azetidinyl]phthalimide as a foam; $[\alpha]_D = +41°$ (c=0.8 in chloroform); MS: 466 (M+).

(b) A solution of 149.3 g (0.32 mol) of N-[(3S,4S)-cis-1-(2,4-dimethoxybenzyl)-4-[(R)-2,2-dimethyl-1,3-dioxolan-4-yl]-2-oxo-3-azetidinyl]phthalimide in 2.5 l of methylene chloride is treated with 34 ml (0.64 mol) of methylhydrazine. The mixture is stirred at 28° overnight, precipitated material is filtered off and the filtrate is evaporated under reduced pressure. The residue is taken up in 1.2 l of ethyl acetate and the suspension obtained is filtered. The filtrate is washed three times with 500 ml of water each time and with 500 ml of sodium chloride solution and dried over sodium sulphate. After evaporation of the solvent, there are obtained 104.3 g (86.8%) of crude (3S,4S)-cis-3-amino-1-(2,4-dimethoxybenzyl)-4-[(R)-2,2-dimethyl-1,3-dioxolan-4-yl]-2-azetidinone which is used in the next step without further purification.

(c) A stirred solution of 1.0 g (3.0 mmol) of (3S,4S)-cis-3-amino-1-(2,4-dimethoxybenzyl)-4-[(R)-2,2-dimethyl-1,3-dioxolan-4-yl]-2-azetidinone and 104 ml (1.2 mol) of butylene oxide in 1.5 l of methylene chloride is treated dropwise with 57.6 ml (0.4 mol) of carbobenzoxy chloride, the mixture is stirred for 1 hour and subsequently evaporated under reduced pressure. The crude material obtained is treated with 2 l of dry ether, there being obtained a crystalline material. There are obtained 122.6 g (84%) of benzyl (3S,4S)-cis-1-(2,4-dimethoxybenzyl)-4-[(R)-2,2-dimethyl-1,3-dioxolan-4-yl]-2-oxo-3-azetidinecarbamate of melting point 115°–116°; $[\alpha]_D = +48°$ (c=0.3 in methanol).

(d) A solution of 160 g (0.34 mol) of benzyl-(3S,4S)-cis-1-(2,4-dimethoxybenzyl)-4-[(R)-2,2-dimethyl-1,3-dioxolan-4-yl]-2-oxo-3-azetidinecarbamate in 1000 ml of tetrahydrofuran and 400 ml of water is stirred at 60° overnight in the presence of 8 g of p-toluenesulphonic acid. The mixture is neutralized with saturated sodium bicarbonate solution and the tetrahydrofuran is evaporated. The aqueous solution is then extracted with 2 l of ethyl acetate. After drying over sodium sulphate and evaporation, there are obtained 142 g (97.2%) of pure benzyl (3S,4S)-cis-4-[(R)-1,2-dihydroxyethyl]-1-(2,4- dimethoxybenzyl)-2-oxo-3-azetidinecarbamate of melting point 177°–178° (methanol).

(e) A solution of 142 g (0.33 mol) of benzyl (3S,4S)-cis-4-[(R)-1,2dihydroxyethyl]-1-(2,4-dimethoxybenzyl)-2-oxo-3-azetidinecarbamate in 1000 ml of tetrahydrofuran is treated dropwise while stirring with a solution or 76.8 g (0.359 mol) of sodium metaperiodate in 600 ml of water. The mixture is stirred for 1 hour, filtered and the filtrate is evaporated under reduced pressure. The residue is taken up in 400 ml of ethyl acetate and washed twice with 100 ml of water each time and with 50 ml of sodium chloride solution. After drying and evaporation, there are obtained 105 g (87.8%) of pure benzyl (3S,4S)-cis-1-(2,4-dimethoxybenzyl)-4-formyl-2-oxo-3-azetidinecarbamate of melting point 145°–147° (from ethyl acetate/hexane); $[\alpha]_D = +13.7°$ (c=1 in chloroform).

(f) 4.27 g (113 mmol) of sodium borohydride are dissolved in 1.6 l of absolute ethanol and cooled to 0°. This solution is treated dropwise with a solution of 90 g (226 mmol) of benzyl (3S,4S)-cis-1-(2,4-dimethoxybenzyl)-4-formyl-2-oxo-3-azetidinecarbamate in 720 ml of ethanol/tetrahydrofuran (1:1). The mixture is stirred at 0° for 2 hours, subsequently treated with 350 ml of saturated aqueous sodium sulphate solution and stirred for 45 minutes. After filtration and evaporation of the solvent, the residue is taken up in 1.5 l of ethyl acetate and washed until the reaction is neutral. After drying over sodium sulphate and partial evaporation, there are obtained 72.2 g (79.6%) of benzyl (3S,4S)-cis-1-(2,4-dimethoxybenzyl)-4-hydroxymethyl-2-oxo-3-azetidinecarbamate in the form of colourless crystals of melting point 138°; $[\alpha]_D = +41.6°$ (c=1 in methanol).

Elemental analysis for $C_{21}H_{24}N_2O_6$: Calculated: C 62.99, H 6.04, N 7.00%. Found: C 62.76, H 6.09, N 6.96%.

IR (KBr) cm$^{-1}$: 1718, 1698, 1615, 1589.

NMR (CDCl$_3$) δ(ppm): 2.45 (1H, dd, OH), 3.55–3.75 (3H, broad, CH—CH$_2$—), 3.79 (6H, s, 2×OCH3), 4.35 (2H, s, N—CH2), 5.08 (2H, s, φ—CH$_2$), 5.02–5.18 (1H, dd, 5 and 9 Hz, H-3), 6.06 (1H, d, 9 Hz, NH), 6.43 (2H, m, Ar), 7.15 (1H, m, Ar), 7.31 (5H, m, C$_6$H$_5$).

MS: 292 (M-BzOH).

(g) A solution of 30 g (74.9 mmol) of benzyl (3S,4S)-cis-1-(2,4-dimethoxybenzyl)-4-hydroxymethyl-2-oxo-3-azetidinecarbamate in 600 ml of methylene chloride is treated at 0°–5° with 21.22 g of chlorosulphonyl isocyanate (2 equivalents). After 15 minutes, the mixture is added dropwise to an aqueous solution, cooled to 5°, of 20.9 g (2.7 equivalents) of sodium sulphite. The mixture is stirred for 2 hours and subsequently diluted with methylene chloride. The organic phase is separated, washed with aqueous sodium chloride solution and dried for 12 hours over sodium sulphate. The organic phase is subsequently treated with magnesium sulphate and stirred for a further 2 hours. After filtration and evaporation of the solvent, the residue is treated with ether, the crystals obtained are filtered off and washed with ether. There are obtained 32.6 g (97%) of (3S,4S)-cis-3-benzyloxycarboxamido-4-carbamoyloxymethyl-1-(2,4-dimethoxybenzyl)-2-azetidinone of melting point 178°–179°; $[\alpha]_D = +84.7°$ (c=0.8 in chloroform).

Elemental analysis for $C_{22}H_{25}N_3O_7$: Calculated: C 59.59, H 5.68, N 9.48%. Found: C 59.17, H 5.69, N 9.37%.

IR (KBr) cm$^{-1}$: 1761, 1708, 1618, 1587.

(h) A suspension of 11.9 g (26.8 mmol) of (3S,4S)-cis-3-benzyloxycarboxamido-4-carbamoyloxymethyl-1-(2,4-dimethoxybenzyl)-2-azetidinone, 14.5 g (53.5 mmol) of potassium peroxodisulphate, 13.98 g (80.3 mmol) of dipotassium hydrogen phosphate and 1.33 g (5.36 mmol) of copper sulphate pentahydrate in 270 ml of acetonitrile and 130 ml of water are heated to 95° for 3.5 hours in an argon atmosphere at a pH value between 6.5 and 7.0 (addition of 10 g of dipotassium hydrogen sulphate from time to time). After cooling and filtration, the aqueous phase is discarded and the organic phase is evaporated. The residue is taken up in ethyl acetate and washed with water and sodium chloride solution. After drying over sodium sulphate, filtration and evaporation of the solvent, the residue is taken up in ether and filtered. The crude crystals (8.9 g) are chromatographed on SiO$_2$ [300 g, 40–63 μm, chloroform/ methanol/ethylacetate (85:10:5)]. There are obtained 5.5 g (70%) of (3S,4S)-cis-3-benzyloxycarboxamido-4-carbamoyloxymethyl-2-axetidinone as colourless crystals; $[\alpha]_D = +61.2°$ (c=1 in methanol); melting point 193°–195°.

Elemental analysis for $C_{13}H_{15}N_3O_5$: Calculated: C 53.24, H 5.16, N 14.33%. Found: C 53.40, H 5.24, N 14.35%.

IR (KBr) cm$^{-1}$: 3414, 3315, 1757, 1701, 1610, 1540, 1498.

NMR (d$_6$-DMSO) δ(ppm): 3.31–4.06 (3H, m, CH—CH$_2$—), 4.95 (1H, dd, 4.5 and 9 Hz, H-3), 5.06 (2H, s, φ-CH$_2$), 6.53 (2H, broad, NH$_2$), 7.35 (5H, s, C$_6$H$_5$), 7.95 (1H, d, 9 Hz, C-3 NH—CO), 8.35 (1H, s, NH—CO).

MS (CI with NH$_3$): 251 (M+H)$^+$—CONH.

(i) 5.4 g (18.4 mmol) of (3S,4S)-cis-3-benzyloxycarboxamido-4-carbamoyloxymethyl-2-azetidinone in 200 ml of absolute dioxan are treated at room temperature with 4.3 g (1.3 equivalents) of pyridine/sulphur trioxide complex. The suspension obtained is stirred for 3 hours, subsequently treated with a further 0.99 g (0.3 equivalents) of pyridine/ sulphur trioxide complex and the mixture is stirred for a furthur hour. After adding a further 1.37 g (0.4 equivalents) of pyridine/sulphur trioxide complex and stirring for a further 2 hours, the solvent is partially removed under reduced pressure and the residue is treated with 110 ml of saturated aqueous sodium bicarbonate solution. The brown solution obtained is left to stand in a refrigerator for 12 hours and the crystals obtained are filtered off. The mother liquor is chromatographed [MCI gel, water/ethanol (1:1 to 9:1)]. After lyophilization, there are obtained 3.5 g (49%) of (3S,4S)-cis-3-benzyloxycarboxamido-4-carbamoyloxymethyl-2-azetidinone-1-sulphonic acid sodium salt as a colourless powder; $[\alpha]_D = +29.6°$ (c=0.5 in water).

Elemental analysis for $C_{13}H_{14}N_3O_8SNa$: Calculated: C 39.50, H 3,57, N 10.63%. Found: C 39.41, H 3.45, N 10.36%.

IR (KBr) cm$^{-1}$: 1798, 1758, 1739, 1693, 1584, 1547.

NMR (d$_6$-DMSO) δ(ppm): 3.9–4.4 (3H, m, CH—CH$_2$), 4.9 (dd, 1H, NH—CH), 5.1 (s, 2H, φ—CH$_2$), 6.4 (2H, broad, NH2), 7.4 (5H, s, C6H5), 8.0 (1H, d, NH).

(k) 3.065 g (7.75 mmol) of (3S,4S)-cis-benzyloxycarboxamido-4-carbamoyloxymethyl-2-azetidinone-1-sulphonic acid sodium salt are dissolved in 180 ml of absolute methanol and hydrogenated in the presence of 1.5 g of 10% palladium/ carbon. The catalyst is removed by filtration and the solution obtained is evaporated. There are obtained 2.02 g (100%) of (3S,4S)-cis-3-amino-4-carbamoyloxymethyl-2-oxo-1-azetidinesulphonic acid sodium salt.

IR (KBr) cm$^{-1}$: 3444, 3207, 1754, 1725, 1611, 1249.

(l) 1.62 g (6.20 mmol) of (3S,4S)-3-amino-4-carbamoyloxymethyl-2-oxo-1-azetidinesulphonic acid sodium salt are dissolved in 180 ml of acetone/water (2:1) and treated with 3.27 g (6.83 mmol) of (Z)-2-(2-amino-4-thiazolyl)-2-[[1-(t-butoxycarbonyl)-1-methylethoxy]imino]-acetic acid 2-benzthiazolyl thioester. The mixture is stirred at room temperature for 12 hours. A further 60 mg (0.12 mmol) of the aforementioned thioester are added thereto and the stirring is continued for a further 3 hours. Acetone is removed under reduced pressure and 50 ml of water are added thereto. The crystals obtained are filtered off and washed with a small amount of water. The mother liquor is partially evaporated (37°, 15 mmHg) and the residue is chromatographed (MCI gel, H$_2$O). After lyophilization, there are obtained 2.28 g (77%) of (3S,4S)-3-[2-amino-4-thiazolyl)-2-(Z)-[[1-(t-butyoxycarbonyl)-1-methylethoxy]imino]acetamido]-4-carbamoyloxymethyl-2-oxo-1-azetidinesulphonic acid sodium salt.

IR (KBr) cm$^{-1}$: 1766, 1723, 1683, 1617, 1531, 1458, 1369.

NMR (d$_6$-DMSO) δ(ppm): 1.35 (15H, s, 5 x CH$_3$), 4.0–4.15 (3H,H-4 and CH$_2$—OCONH$_2$), 5.25 (1H, dd, H-3), 6.5 (2H, broad, CONH$_2$), 6.7 (1H, s, H-thiazole), 7.25 (2H, s, NH$_2$), 8.9 (1H, d, CO—NH).

(m) 2.2 g (3.98 mmol) of (3S,4S)-3-[2-amino-4-thiazolyl)-2-(Z)-[[1-(t-butyoxycarbonyl)-1-methylethoxy]imino]acetamido]-4-carbamoyloxymethyl-2-oxo-1-azetidinesulphonic acid sodium salt are treated with 5 ml of trifluoroacetic acid while cooling with ice. The ice-bath is removed and the mixture is stirred at room temperature for 30 minutes. Excess trifluoroacetic acid is removed under reduced pressure (20° C., 15 mmHg). The crystals obtained are filtered off, washed with ether and dried under greatly reduced pressure. After aqueous reverse-phase chromatography, there are obtained after lyophilization 1.51 g (76.6%) of (3S,4S)-3-[(Z)-2-(2-amino-4-thiazolyl)-2-[[1-carboxy-1-methylethoxy]imino]acetamido]-4-carbamoyloxymethyl-2-oxo-1-azetidinesulphonic acid [α]$_D$= +35.7° (c=0.3 in water).

Elemental analysis for C$_{14}$H$_{18}$N$_6$O$_{10}$S$_2$: Calculated: C 34.01, H 3.67, N 17.00%. Found: C 34.52, H 3.72, N 16.63%.

IR (KBr) cm$^{-1}$: 1764, 1722, 1680, 1637.

NMR (d$_6$-DMSO) δ(ppm): 1.5 (6H, s, 2 x CH$_3$), 4.00–4.20 (3H, CH—CH$_2$), 5.35 (1H, dd, 4.5 and 9 Hz, H-3), 6.50 (3H, broad, NH$_3$+ or COOH, CONH$_2$), 6.90 (1H, s, thiazole-5H), 9.15 (1H, d, 9 Hz, CONH).

The 2-(2-amino-4-thiazolyl)-2-[[(Z)-1-(t-butoxycarbonyl)-1-methylethoxy]imino]-acetic acid 2-benzthiazolyl thioester used as the reagent in paragraph 1) can be prepared as follows:

(n) 43 g (200 mmol) of 2-(2-amino-4-thiazolyl)-2-(Z)-hydroxyimino-acetic acid ethyl ester are dissolved in 1.2 l of dimethylformamide. In a nitrogen atmosphere 89.2 g (400 mmol) of t-butyl 2-bromo-2-methyl-propionate are gradually added thereto, followed by 110.6 g (800 mmol) of finely powdered potassium carbonate. The mixture is stirred at 45° for 12 hours. After cooling to room temperature, 4 l of water are added thereto and the mixture is extracted with 3.5 l of ethyl acetate. The organic phase is washed three times with 2 l of water. The water is again extracted with 1.5 l of ethyl acetate. The combined ethyl acetate solutions are dried with magnesium sulphate and evaporated to dryness. After recrystallization from ether, there are obtained 61.4 g (85.9%) of 2-(2-amino-4-thiazolyl)-2-[[(Z)-1-(t-butoxycarbonyl)-1-methylethoxy]imino]-acetic acid ethyl ester of melting point 172°.

(o) 240 g (671.5 mmol) of 2-(2-amino-4-thiazolyl)-2-[[(Z)-1-(t-butoxycarbonyl)-1-methylethoxy]imino]-acetic acid ethyl ester are stirred at 50° for 12 hours in 1.3 l of methanol and 1.34 l of 1N aqueous sodium hydroxide. The methanol is removed by evaporation and the aqueous phase is washed twice with 1 l of ethyl acetate. The product crystallizes out after adding 1.34 l of 1N aqueous hydrochloric acid. After cooling to 0°, the crystals are filtered off, washed successively with water, acetonitrile and ether and dried at 40° under reduced pressure. The thus-obtained product crystallizes with 12% water and is stirred in acetonitrile for 2 hours in order to removed the water. After filtration and drying under reduced pressure at 40°, there are obtained 177.7 g (80.3%) of 2-(2-amino-4-thiazolyl)2-[[(Z)-1-(t-butoxycarbonyl)-1-methylethoxy]imino]-acetic acid of melting point 178°–179° (water content 0.4%).

(p) 28.8 g (86.4 mmol) of 2-(2-amino-4-thiazolyl)-2-[[(Z)-1-(t-butoxycarbonyl)-1-methylethoxy]imino]-acetic acid are dispersed in 360 ml of acetonitrile. 14.4 ml (130.5 mmol) of N-methylmorpholine are added thereto while stirring. After 10 minutes, 34.6 g (103.5 mmol) of 2,2-dithio-bis-benzthiazole are added thereto and the suspension obtained is cooled to 0°. After adding 20.2 ml (117 mmol) of triethylphosphite (slow addition within 2 hours), the suspension is stirred at 0° for 12 hours. The product is filtered off, washed successively with cold acetonitrile, diisopropyl ether and petroleum ether and dried at room temperature under reduced pressure. There is obtained 2-(2-amino-4-thiazolyl)-2-[[(Z)-1-(t-butoxycarbonyl)-1-methylethoxy]imino]-acetic acid 2-benzthiazolyl thioester (33.7 g=81.5%) of melting point 139°–140°.

EXAMPLE 16

(a) 17 g (42.7 mmol) of benzyl (3S,4S)-cis-1-(2,4-dimethoxybenzyl)-4-formyl-2-oxo-3-azetidinecarbamate [Example 13 e)] are dissolved in 100 ml of methylene chloride and 100 ml of n-propanol. This solution is treated with 3.5 g (50.3 mmol) of hydroxylamine hydrochloride and then with 4.2 ml (52 mmol) of pyridine. The mixture is heafed under reflux conditions for 2 hours. The methylene chloride is subsequently distilled off and a solution of 6.3 g (57 mmol) of selenium dioxide in 100 ml of n-propanol is added dropwise. The mixture is heated under reflux conditions for 2 hours, cooled to room temperature and filtered. The solution obtained is evaporated under reduced pressure. The oil obtained is dissolved in 100 ml of n-propanol and evaporated. This procedure is repeated twice. The resulting partially crystalline residue is taken up in 250 ml of methylene chloride and washed successively twice with in each case 200 ml of water and sodium chloride solution. After drying over sodium sulphate, filtration and evaporation of the solvent, the residue is taken up in 70 ml of n-propanol. The solution is left to stand in a refrigerator for 12 hours. There are obtained 16.4 g (97%) of benzyl (3S,4S)-cis-1-(2,4-dimethoxybenzyl)-4-cyano-2-oxo-3-azetidinecarbamate of melting point 152°–153°; [α]$_D$= +10.6° (c=1 in chloroform).

MS: 395 (M+).

(b) 15.72 g (58.2 mmol) of potassium peroxodisulphate and 9.5 g (54.8 mmol) of dipotassium hydrogen phosphate are dissolved in 480 ml of water. The solution is heated to 80° and treated with a solution of 1.2 g of copper sulphate in 10 ml of water. The suspension obtained is diluted with 180 ml of acetonitrile and treated dropwise with a solution of 14.4 g of benzyl (3S,4S)-cis-1-(2,4-dimethoxybenzyl)-4-cyano-2-oxo-3-azetidinecarbamate in 300 ml of acetonitrile. The mixture is heated under reflux conditions for 2.5 hours, subsequently cooled, filtered and partially evaporated. The resulting oily aqueous solution is extracted with ethyl acetate and the organic phase is washed successively three times with aqueous saturated sodium bicarbonate solution, water and sodium chloride solution. After drying and evaporation of the solvent, the oil obtained is chromatographed on silica gel [230–400 mesh, elution agent ethylacetate/n-hexane (1:1)]. There are obtained 6.1 g (68.3%) of benzyl (3S,4S)-cis-4-cyano-2-oxo-3-azetidinecarbamate of melting point 163°–165°.

MS: 245 (M+).

(c) 6.16 g (25 mmol) of benzyl (3S,4S)-cis-4-cyano-2-oxo-3-azetidinecarbamate are dissolved in 45 ml of dimethyl sulphoxide and treated with 5.58 ml of 30% aqueous hydrogen peroxide. After the temperature has fallen to 25°, the mixture is treated with 5 ml of aqueous 1N sodium hydroxide solution. The temperature rises to 55°. A precipitate results after stirring for 45 minutes. 20 ml of ethyl acetate are added thereto and the crystals obtained are filtered off. The crystals are washed with aqueous ethanol and absolute ether. There are obtained 2.48 g (37.5%) of benzyl (3S,4S)-4-carbamoyl-2-oxo-3-azetidinecarbamate of melting point 248°–249°; $[\alpha]_D = +13°$ (c=1 in dimethyl sulphoxide).

The mother liquor is partially evaporated, a further 0.53 g of product being isolated. The thus-obtained mother liquor is diluted with water and chromatographed on MCI gel [ethanol/water (3:7) as the elution agent]. The total yield of end product is 3.5 g (53%).

(d) 7.9 g (30 mmol) of benzyl (3S,4S)-4-carbamoyl-2-oxo-3-azetidinecarbamate are suspended in 470 ml of absolute dioxan and treated with 6.2 g (39 mmol) of pyridine/ sulphur trioxide complex. The suspension obtained is stirred at room temperature for 2 hours, subsequently treated with 1.41 g (8.8 mmol) of pyridine/sulphur trioxide complex and the mixture is stirred for a furthur hour. After adding 1.90 g (12 mmol) of pyridine/sulphur trioxide complex and stirring for a further 2 hours, the solvent is removed by evaporation under reduced pressure and the residue is taken up in 200 ml of water. The resulting aqueous solution is treated with 15 g (44.24 mmol) of tetrabutylammonium hydrogen sulphate. This aqueous solution is extracted twice with 250 ml of methylene chloride each time and the methylene chloride extracts are dried over sodium sulphate. After evaporation of the solvent, the oily residue obtained is dissolved in 150 ml of absolute methanol and hydrogenated over 2.5 g of 10% palladium/carbon. The catalyst is filtered off, the solution is evaporated and the residue is dissolved in a solution of 70 ml of formic acid in 100 ml of methylene chloride. After 2 hours, the solvent is removed by evaporation and the residue is treated with 25 ml of water. There are obtained 2.3 g (36%) of (3S,4S)-3-amino-4-carbamoyl-2-oxo-1-azetidinesulphonic acid. The mother liquor is chromatographed on MCI gel elution agent water/ethanol (1:0 to 9:1)], a further 420 mg of product being obtained. The total yield is 2.7 g (43.3%).

IR (KBr) cm$^{-1}$: 1779, 1696, 1633, 1485, 1288, 1250.

NMR (d$_6$-DMSO) δ(ppm): 4.43 and 4.72 (2×1H, 2d, 6Hz, CH—CH), 7.88 (2H, d, broad, NH2), 8.59 (3H, broad, NH$_3$+).

(e) From (3S,4S)-3-amino-4-carbamoyl-2-oxo-1-azetidinesulphonic acid and 2-(2-amino-4-thiazolyl)-2-(Z)-methoxy-imino-acetic acid 2-benzthiazolyl thioester there is obtained in analogy to Example 13) (3S,4S)-3-[(Z)-2-(2-amino-4-thiazolyl)-2-(methoxyimino)-acetamido]-4-carbamoyl-2-oxo-1-azetidinesulphonic acid sodium salt.

Elemental analysis for $C_{10}H_{11}N_6O_7S_2Na$: Calculated: C 28.99, H 2.68, N 20.68%. Found: C 31.20, H 3.26, N 16.41%.

IR (KBr) cm$^{-1}$: 3282, 1790, 1640, 1612, 1527, 1260, 1230.

NMR (d$_6$-DMSO) δ(ppm): 3.85 (3H, s, OCH$_3$), 4.3 (1H, d, 6 Hz, CH—CONH$_2$), 5.30 (1H, dd, 6 and 9 Hz, NH—CH), 6.95 (1H, s, S—CH=), 7.40 (2H, d, 18 Hz, CONH$_2$), 9.25 (1H, d, 9 Hz, NH—CO).

The 2-(2-amino-4-thiazolyl)-2-(Z)-methoxyiminoacetic acid 2-benzthiazolyl thioester used as the reagent in paragraph (e) can be prepared as follows:

(f) 3.93 g of triphenylphosphine and 5 g of dithiobis-benzthiazole are suspended in 50 ml of dichloromethane and stirred at room temperature for about 30 minutes. After cooling to 0°, 2 g of 2-(2-amino-4-thiazolyl)-2-(Z)-methoxyimino-acetic acid are added and the mixture is stirred at 0° for 3 to 4 hours. For the working-up, the undissolved material is filtered off under suction and washed with a small amount of cold methylene chloride. The solid is suspended in 25 ml of ethyl acetate, stirred at 0° for 30 minutes, again suction filtered and washed with ethyl acetate. After recrystallization from tetrahydrofuran/dichloromethane, there is obtained 2-(2-amino-4-thiazolyl)-2-(Z)-methoxyimino-acetic acid 2-benzthiazolyl thioester of melting point 128°–130°.

EXAMPLE 17

(a) 265 mg (0.5 mmol) of (Z)-2-(2-amino-4-thiazolyl)-2-[[(p-nitrobenzyloxycarbonyl)methoxy]imino]-acetic acid 2-benzthiazolyl thioester and 104 mg (0.5 mmol) of (3S,4S)-3-amino-4-carbamoyl-2-oxo-1-azetidinesulphonic acid [from Example 14 d)] are suspended in 2.5 ml of absolute acetone and treated with 0.15 ml (1.1 mmol) of triethylamine. After 30 minutes, the suspension changes to a yellow solution. After 24 hours at room temperature, the solution is evaporated and the residue is subjected to DCCC droplet counter current chromatography: rising droplets in the mixture chloroform/methanol/water (7:13:8)]. The interesting fractions are evaporated and the residue is lyophilized. There is obtained 0.139 g (41%) of (3S,4S)-3-[(Z)-2-(2-amino-4-thiazolyl)-2-[[(p-nitrobenzyloxycarbonyl)-methoxyimino]acetamido]-4-carbamoyl-2-oxo-1-azetidinesulphonic acid triethylamine salt.

NMR (D$_2$O) δ(ppm): 1.31 (t, J=7.5, 9H), 3.24 (q, J=7.5, 6H), 4.95 (d, J=6.0, 1H), 4.95 (s, 2H), 5.34 (s, 2H), 5.69 (d, J=6.0, 1H), 6.98 (s, 1H), 7.49 (d, J=9.0, 2H), 8.16 (d, J=9.0, 2H)

IR (KBr) cm$^{-1}$: 3333 (42%), 1773 (26%), 1687 (20%), 1608 (42%), 1348 (27%), 1277 (22%), 1248 (26%), 1046 (19%).

$C_{18}H_{17}N_7O_{11}S_2 + C_6H_{15}N$ (672.698): Calculated: C 42.85, H 4.80, N 16.66, S 9.53. Found: C 41.22, H 4.81, N 16.13, S 9.45, H$_2$O 1.84%.

(b) 336 mg (0.5 mmol) of (3S,4S)-3-[(Z)-2-(2-amino-4-thiazolyl)-2-[[(p-nitrobenzyloxycarbonyl)-methoxyimino]-acetamido]-4-carbamoyl-2-oxo-1-azetidinesulphonic acid triethylamine salt are dissolved in 20 ml of methanol and hydrogenated with 150 mg of 5% palladium on infusorial earth at room temperature for 3–4 hours. The catalyst is removed by filtration and the solution is evaporated. The residue is dissolved in a small amount of saturated aqueous sodium bicarbonate solution and chromatographed on Amberlite XAD-2 (eluant: water, subsequently 40% ethanol in water). After lyophilization, there are obtained 150 mg (65%) of (3S,4S)-3-[(Z)-2-(2-amino-4-thiazolyl)-2-[(carboxymethoxy)imino]acetamido]-4-carbamoyl-2-oxo-1-azetidinesulphonic acid sodium salt.

IR: 3421, 1769, 1731, 1690 cm$^{-1}$.

The 2-(2-amino-4-thiazolyl)-2-[[(Z)-(p-nitrobenzyloxycarbonyl)methoxy]imino]-acetic acid 2-benzthiazolyl thioester used as the starting material in paragraph (a) can be prepared as follows:

(c) 6.1 g (25 mmol) of 2-(2-amino-4-thiazolyl)-2-(Z)-hydroxyimino-acetic acid t-butyl ester are dispersed in 250 ml of dry acetonitrile. There are now added thereto at room temperature while stirring 13.7 g (50 mmol) of 4-nitrobenzyl bromoacetate and 12.9 ml (75 mmol) of N-ethyldiisopropylamine. 5 minutes later 7.5 g (50 mmol) of sodium iodide are added thereto. The mixture is stirred at room temperature for 3.5 hours in an argon atmosphere. The solvent is subsequently removed by evaporation and the residue is diluted with 500 ml of ethyl acetate. The resulting solution is washed four times with a total of 2 l of water. The water is extracted with 300 ml of ethyl acetate and the combined ethyl acetate solutions are dried over sodium sulphate and evaporated to dryness. After crystallization from ethyl acetate/hexane, there are obtained 8.2 g (75%) of 2-(2-amino-4-thiazolyl)-2-[[(p-nitrobenzyloxycarbonyl)methoxy]imino]-acetic acid t-butyl ester of melting point 146.8° (decomposition).

(d) 5.0 g (11.4 mmol) of 2-(2-amino-4-thiazolyl)-2-[[(Z)-(p-nitrobenzyloxycarbonyl)methoxy]imino]-acetic acid t-butyl ester are stirred in 86 ml of acetic acid and treated with 5.2 ml (38.4 mmol) of boron trifluoride etherate. The resulting solution is stirred at room temperature for 5 hours and subsequently poured into 260 ml of water. The precipitate obtained is filtered off and dried at 40° C. under reduced pressure. There are obtained 3.5 g (80%) of 2-(2-amino-4-thiazolyl)-2-[[(p-nitrobenzyloxycarbonyl)methoxy]imino]-acetic acid of melting point about 175° (decomposition).

(e) 1.9 g (0.5 mmol) of 2-(2-amino-4-thiazolyl)-2-[[(Z)-(p-nitrobenzyloxycarbonyl)methoxy]imino]-acetic acid are dispersed in 30 ml of acetonitrile (dried with a 3 Å molecular sieve). This suspension is treated with 1.4 ml (12.7 mmol) of N-methylmorpholine while stirring, followed by 2.0 g (6.0 mmol) of 2,2-dithio-bis-benzthiazole and 1.14 ml (6.7 mmol) of triethylphosphite. After stirring at room temperature for 1 hour, the mixture is cooled to 0° C. and filtered. The filtrate is evaporated and the residue is crystallized from methylene chloride. There are obtained 1.03 g (39%) of 2-(2-amino-4-thiazolyl)-2-[[(Z)-(p-nitrobenzyloxycarbonyl)methoxy]imino]-acetic acid 2-benzthiazolyl thioester of melting point 124°–126°.

EXAMPLE 18

(a) In analogy to Example 15(a), from 2-(2-amino-4-thiazolyl)-2-[[(Z)-(p-nitrobenzyloxycarbonyl)methoxy]imino]-acetic acid 2-benzthiazolyl thioester and (3S,4S)-3-amino-4-carbamoyloxy-methyl-2-oxo-1-azetidinesulphonic acid there is obtained (3S,4S)-3-[(Z)-2-(2-amino-4-thiazolyl)-2-[[(p-nitrobenzyloxycarbonyl)methoxyimino]acetamido]-4-carbamoyloxy methyl-2-oxo-1-azetidinesulphonic acid sodium salt.

Elemental analysis for $C_{19}H_{18}N_7O_{12}S_2Na$: Calculated: C 36.60, H 2.91, N 15.73, S 10.28%. Found: C 37.00, H 2.88, N 15.74, S 10.45%.

IR (KBr) cm$^{-1}$: 3353, 1761, 1729, 1524, 1348.

NMR (d$_6$-DMSO) δ(ppm): 4.0–4.2 (3H, m, CH—CH$_2$), (2H, s, $\phi$—CH$_2$), 5.30 (1H, dd, NH—CH—), 5.32 (2H, s, O—CH$_2$), 6.70 (2H, broad, NH$_2$), 6.9 (1H, s, S—CH=), 7.10 (2H, broad, NH$_2$), 7.70 and 8.2 (2 × 2H, 2d, 2×3 Hz, Ar), 9.5 (1H, d, 9 Hz, NHCO)

(b) 270 mg (0.43 mmol) of (3S,4S)-3-[(Z)-2-(2-amino-4-thiazolyl)-2-[[(p-nitrobenzyloxycarbonyl)methoxyimino]-acetamido]-4-carbamoyloxymethyl2-oxo-1-azetidinesulphonic acid sodium salt are dissolved in 30 ml of methanol and hydrogenated over 5% palladium on infusorial earth (150 mg). The catalyst is filtered off and the solvent is evaporated. The residue is taken up in 2.5 ml of water and washed twice with ethyl acetate. The aqueous phase is chromatographed (reverse-phase, water as the elution agent). There are obtained 115 mg (54%) of (3S,4S)-3-[(Z)-2-(2-amino-4-thiazolyl)-2-[(carboxymethoxy)imino]acetamido]-4-carbamoyloxymethyl-2- oxo-1-azetidinesulphonic acid sodium salt.

Elemental analysis for $C_{12}H_{13}N_6O_{10}S_2Na$: Calculated: C 29.51, H 2.68, N 17.21%. Found: C 27.09, H 2.35, N 15.33%.

IR (KBr) cm$^{-1}$: 3434, 1766, 1718, 1669, 1613, 1533, 1278, 1251.

MNR (d$_6$-DMSO) δ(ppm): 3.90–4.15 (3H, m, CH—CH$_2$), 4.30 (2H, s, CH$_2$—COOH), 5.20 (1H, dd, 5 and 9 Hz, NH—CH), 6.6 (2H, broad, NH$_2$), 6.78 (1H, s, S—CH=), 7.13 (2H, s, NH$_2$), 10.90 (1H, d, 9 Hz, CONH).

EXAMPLE 19

(3S,4S)-3-[(Z)-2-[2-amino-4-thiazolyl)-2-[[1-carboxy-1-methylethoxy]imino]acetamido]-4-carbamoyl-2-oxo-1-azetidinesulphonic acid is obtained in analogy to Example 15 and 16.

Elemental analysis for $C_{13}H_{16}N_6O_9S_2$ Calculated: C 33.62, H 3.47, N 18.10%. Found: C 33.24, H 3.18, N 17.94%.

IR (KBr) cm$^{-1}$: 3332, 3208, 2552, 1780, 1684, 1638, 1279, 1188.

NMR (d$_6$DMSO)δ(ppm): 1.44 (6H, s, 2 x CH$_3$), 4.34 (1H, d, 6 Hz, CH—CONH$_2$), 5.33 (1H, dd, 6 and 9 Hz, NH—CH—), 6.96 (1H, s, S—CH=), 7.40 (2H, broad, d, 7 Hz, CONH$_2$), 8.95 (1H, d, 9 Hz, CONH).

UV (EtOH): 292 nm (6846), 240 nm (12232).

What is claimed:

1. An optically uniform compound of the formula

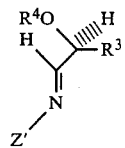

III wherein R$^3$ and R$^4$ each are joined with one another together with the CHO to which they are attached to form a substituted or unsubstituted 5 or 6-membered heterocyclic ring which contains a further oxygen atom not directly linked with the center of chirality and which can be substituted by lower alkyl, lower alkoxy, oxo or spirocyclo-lower alkyl, and Z' is a readily cleavable protecting group selected from the group consisting of 2,4- or 3,4-di-(lower alkoxy)-phenyl, 2,4- or 3,4-di-(lower alkoxy)-benzyl, di-(4-(lower alkoxy)-phenyl) methyl or 4-(lower alkoxy)-phenyl, and the corresponding optical antipodes thereof.

2. The compound of the formula

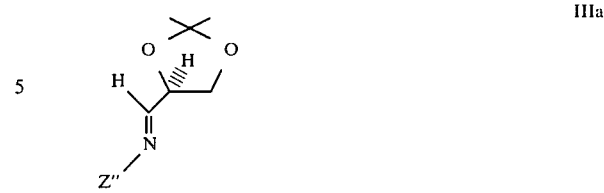

IIIa wherein Z" is 2,4- or 3,4-di-(lower alkoxy)benzyl, di-[4-(lower alkoxy) phenyl]-methyl or 4-(lower alkoxy)-phenyl,
and the corresponding optical antipodes thereof.

3. The compound: Isopropylidene-L-glyceraldehyde (2,4-dimethoxybenzyl)imine.

4. The compound: Isopropylidene-L-glyceraldehyde (3,4-dimethoxybenzyl)imine.

* * * * *